United States Patent
Demmer et al.

[11] Patent Number: 6,001,974
[45] Date of Patent: Dec. 14, 1999

[54] METHOD OF SEPARATING ALBUMIN FROM SERUM BY ION-EXCHANGE CHROMATOGRAPHY WITH MEMBRANE ADSORBERS

[75] Inventors: Wolfgang Demmer, Göttingen; Heinrich Klaus Gebauer, Jülich; Maria-Regina Kula, Niederzier; Dietmar Nussbaumer, Göttingen; Jörg Thoemmes, Bonn, all of Germany

[73] Assignee: Sartorius AG, Germany

[21] Appl. No.: 09/041,082

[22] Filed: Mar. 10, 1998

[30] Foreign Application Priority Data

Oct. 17, 1995 [DE] Germany ............... 195 38 625

[51] Int. Cl.$^6$ ............................................. C07K 14/765
[52] U.S. Cl. ........................ 530/364; 530/363; 530/412; 530/416; 530/417
[58] Field of Search ................... 530/364, 363, 530/412, 416, 417

[56] References Cited

U.S. PATENT DOCUMENTS 4,086,222  4/1978  Lindquist et al. ............... 530/364
5,728,553  3/1998  Goodey et al. ............... 435/69.6

OTHER PUBLICATIONS

Freitag et al, *J. Chromatogr. A.*, vol. 728, issue 1–2, pp. 129–137, 1986.

*Primary Examiner*—Cecilia Tsang
*Assistant Examiner*—Abdel A. Mohamed
*Attorney, Agent, or Firm*—Chernoff, Vilhauaer, McClung & Stenzel, LLP

[57] ABSTRACT

A method of separating albumin from serum by ion exchange chromatography with membrane adsorbers characterized by high productivity and yields of high purity albumin. The separation of the albumin is carried out on highly basic anion exchange membranes and on highly acidic cation exchange membranes. The albumin fraction can be eluted from the anion exchange membrane such that it can be fed directly to the cation exchange membrane without any special conditioning and the albumin can be extracted therefrom as an end product.

3 Claims, 1 Drawing Sheet

METHOD OF SEPARATING ALBUMIN FROM SERUM BY ION-EXCHANGE CHROMATOGRAPHY WITH MEMBRANE ADSORBERS

BACKGROUND OF THE INVENTION

Albumin from human plasma serum has broad application in the field of medicine. For this reason, there is a high demand for high purity albumin, i.e., on the order of at least 97% pure. Besides the isolation of albumin by cold ethanol precipitation, use of chromatographic treatment processes has received some attention. See, for example, Curling, "Albumin Purification by Ion Exchange Chromatography", pages 77 to 91, in *Methods of Plasma Protein Fractionation*, Academic Press, London (1980). In such protein chromatography separation methods, the separation capacity of the conventional particulate adsorber materials generally used is limited by pore-diffusion effects. Chromatographic processes using membrane adsorbers, on the other hand, by virtue of their microporous structure, permit substantially greater transfer of the proteins to the adsorbing sites within the membrane adsorber, thereby allowing an increased separation capacity.

Lacoste-Bourgeacq et al., in 32 *Chromatographia* 27 (1991), describe the chromatographic separation of albumin from fraction IV of the Kistler and Nitschmann fractionation of blood plasma on weakly basic and strongly acidic membrane adsorbers. A drawback to this known process is that the albumin fraction, following its elution from the weakly basic membrane adsorber, must undergo a separate treatment step before it can be fed to the strongly acid membrane adsorber. Not surprisingly, the process is very inefficient in that albumin is obtained in a relatively low yield and purity of 66% and 90%, respectively.

There is therefore still a need in the art of albumin recovery for a simple method leading to high yields and purity.

SUMMARY OF THE INVENTION

The present invention provides for the separation of albumin with strongly basic anion and strongly acidic cation ion exchange membranes. Quite surprisingly it has been found that the albumin fraction eluted from the anion exchange membrane may be transferred directly to the cation exchange membrane without separate treatment, and albumin can be obtained from said fraction in a yield of at least 84% and with a purity of at least 97%. In addition, it has been found that immunoglobulin (IgG) may be removed with the same buffer solution that is subsequently used to elute albumin from the anion exchange membrane, allowing the pH and ionic strength of the buffer to be so chosen, that virtually no albumin is eluted with the IgG or is otherwise lost in the procedure.

To conduct the process, partially defibrinated fresh plasma is first centrifuged to separate particulates. Then sterile filtration is carried out by a micro filtration membrane, followed by plasma desalination by gel filtration. After centrifugal separation of euglobulin, the plasma is contacted with the anion exchange membrane and eluted by adjusting the eluting buffer's pH and ionic strength. Without further manipulation, the elute is fed directly to the cation exchange membrane. In the cation exchanger, albumin is eluted by again adjusting the pH and ionic strength of the eluting buffer solution. This eluate contains the desired albumin fraction.

DETAILED DESCRIPTION OF THE PREFERRED EMBODIMENT

Figure 1:
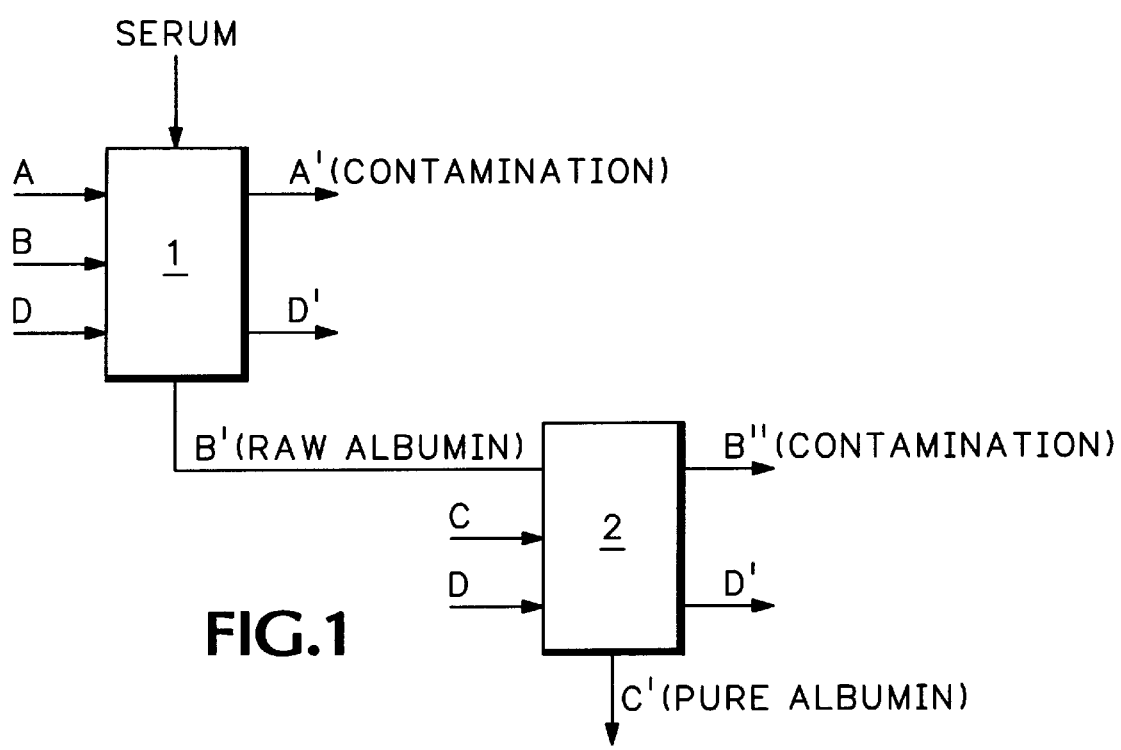
FIG. 1 is a schematic flow diagram of the process of the present invention.

Referring to FIG. 1, strongly basic anion exchange membranes are situated in module 1 while strongly acidic cation exchange membranes are in module 2. Arrows A, B, C and D on the left side of modules 1 and 2 represent the entry of eluting buffer solutions, while arrows A', B', B", C' and D' on the right and under sides of the modules represent the discharge of the buffer solutions to form eluates subsequent to their transfer through the membranes adsorbers. The substance with which the buffer is laden is named in parentheses.

EXAMPLE

Approximately 250 mL of frozen preserved human serum containing 39 g/L a bumin and 60 g/L total protein and having a conductivity of 11.3 mS/cm and a pH of 7.8 was pretreated by thawing and centrifuging at 15,000 G for 40 minutes and at 4° C., then filtered with a micro-filtration membrane having a pore size of 0.45 $\mu$m (MINISTART™ N from Sartorius AG of Gottingen, Germany and commercially available from Sartorius Corporation Separations Division of Edgewood, N.Y.), followed by desalination by gel filtration and recharging with a buffer solution of 25 mM of sodium acetate (pH 7.0), leaving 290 mL of raw albumin-containing solution having a conductivity of 1.8 mS/cm and a pH of 7.5.

The pH of this solution was then adjusted to 5.4 with acetic acid, thereby forming a euglobulin. The sample was again centrifuged at 15,000 G for 40 minutes, and the supernatant was retrieved and frozen at −18° C. This albumin-containing supernatant had a total protein content of 37.5 g/L, an albumin concentration of 26 g/L and a conductivity of 1.8 mS/cm. A portion of this frozen serum-containing supernatant was then thawed at 4° C. and centrifuged for 20 minutes at 4° C. at 12,000 G to obtain the sample to be treated.

Module 1 comprised two strongly basic SARTOBIND™ Q 100 anion exchange membrane adsorber modules (Sartorius AG, Gottingen, Germany and commercially available from Sartorius Corporation Separations Division of Edgewood, N.Y.; see Sartorius Laboratory Separations 1997 product catalog entitled "Membrane Separations Products for Enhanced Productivity in the Biotechnology Laboratory") placed in series. The module was brought into equilibrium by flushing with 65 mL of a buffer A (composition: 25 mM sodium acetate; pH=5.4; conductivity=1.8 mS/cm; ion strength I=0.025 mol/L). Then 2.9 mL of the sample, representing 18.9 mg albumin/mL of adsorber solution, was pumped through module 1 at a flow rate of 24 mL/min (1.22 cm/min). Subsequently, 28 mL of the same buffer A was pumped through the module. The eluate A' contained contamination, IgG in particular. Thereafter, 32 mL of buffer B (composition: 50 mM sodium acetate; pH=4.5; conductivity=3.6 mS/cm; I=005 mol/L) was pumped through module 1, whereupon 32 mL of raw human serum albumin (Roh-HSA) was eluted in eluate B' having an albumin concentration of 2.15 g/L. To regenerate the adsorption capacity of module 1, 28 mL of buffer D (composition: 50 mM sodium acetate; pH=4.2+0.5 M NaCl; conductivity=45 mS/cm, I=0.5 mol/L) was pumped through module 1, producing another fraction D' containing contamination. This completed one cycle, lasting 6.5 minutes. Subsequently, 65 mL buffer A was again pumped through module 1 to begin a new cycle.

To establish initial equilibrium, 65 mL of buffer B was pumped into module 2, comprising two SARTOBIND™ S 100 strongly acidic cation exchange membrane adsorber modules (Sartorius AG, Gottingen, Germany and commercially available from Sartorius Corporation, Separations Division of Edgewood, N.Y.; see Sartorius Laboratory Separations 1997 product catalog entitled "Membrane Separations Products for Enhanced Productivity in the Biotechnology Laboratory") connected in series and run with a flow rate of 24 mL/min (1.22 cm/min). Then, 26 mL of the Roh-HSA elute B' was directed to module 2 (13.9 mg/mL of adsorber solution). Next, 20 mL of buffer B was pumped in. Further contaminants were eluted in this the so-formed fraction B". Subsequently, 50 mL of buffer C (composition: 25 mM sodium acetate; pH=5.4+150 mM NaCl; conductivity=19.8 mS/cm; I=0.2 mol/L) was pumped through the module. In this fraction, 48.2 mL of pure HSA was eluted as the end product in eluate C' (albumin concentration=1.1 g/L), completing an 8-minute cycle. To regenerate the adsorption capacity of module 2, 30 mL of buffer D was pumped in to begin a new cycle. More than 100 cycles were completed in both modules with virtually no deviation in the yield and purity obtained.

Determination of the total protein content in the fractions was carried out in accordance with the Bradford procedure set forth in 72 *Anal. Biochem.* 248 (1976). Albumin content was calculated in accordance with the protocol of Ness et al. in 12 *Clin. Chim. Acta* 532 (1965). With purity being defined as the actual measured ratio of HSA to total protein content, the purity and yields achieved by the separation exemplified above are shown in the table below.

|  | Module 1 (SARTIBIND ™ Q) | Module 2 (SARTOBIND ™ Q) |
| --- | --- | --- |
| Yield | 87% | 95% |
| Purity | 96% | 98% |

As is apparent, the process of the present invention enables an isolation of albumin from serum with a purity of at least 97%. The productivity of the process may be stated as ca. 160 g albumin/(L adsorber·h) for the anion exchange membrane and 96 g albumin/(L adsorber·h) for the cation exchange membrane. The flow rates used in this Example (1.2 cm/min) were comparatively low. These flow rates can, with no diminution of separating capacity, be increased to 20 cm/min, preferably 10–15 cm/min, depending upon module configuration.

Since the capacity and separation efficiency of the system practically does not change, the capacities of the anion and cation exchanger membrane adsorber modules can be so tuned to one another, that the process may be run continuously through cyclic repetition of the process steps.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

We claim:

1. A process for separating albumin from serum comprising:

(a) delivering albumin-containing serum to a strongly basic anion exchange membrane adsorber;

(b) contacting said anion exchange membrane adsorber with a first buffer solution to separate a first fraction containing contaminants;

(c) contacting said anion exchange membrane adsorber with a second buffer solution to form a first eluate containing raw albumin;

(d) delivering said first eluate to a strongly acidic cation exchange membrane adsorber;

(e) contacting said cation exchange membrane adsorber with said second buffer solution to form a second fraction containing contaminants;

(f) eluting substantially pure albumin from said cation exchange membrane adsorber with a third buffer solution.

2. The process of claim 1, including contacting said anion and cation exchange membrane adsorbers with said first buffer solution.

3. The process of claim 1 or 2 conducted in cyclic repetition.

\* \* \* \* \*

UNITED STATES PATENT AND TRADEMARK OFFICE
CERTIFICATE OF CORRECTION

PATENT NO.    : 6,001,974    Page 1 of 1
DATED         : December 14, 1999
INVENTOR(S)   : Demmer et al.

It is certified that error appears in the above-identified patent and that said Letters Patent is hereby corrected as shown below:

Column 2,
Line 16, change "a bumin" to read -- albumin --
Line 55, change "005 mol" to read -- 0.05 mol --

Signed and Sealed this

Twenty-third Day of December, 2003

JAMES E. ROGAN
*Director of the United States Patent and Trademark Office*